United States Patent
Brown

(10) Patent No.: US 6,966,906 B2
(45) Date of Patent: Nov. 22, 2005

(54) DEFLECTION MECHANISM FOR A SURGICAL INSTRUMENT, SUCH AS A LASER DELIVERY DEVICE AND/OR ENDOSCOPE, AND METHOD OF USE

(76) Inventor: Joe Denton Brown, 8317 Front Beach Rd., Ste. 15, Panama City Beach, FL (US) 32407

( * ) Notice: Subject to any disclaimer, the term of this patent is extended or adjusted under 35 U.S.C. 154(b) by 253 days.

(21) Appl. No.: 10/153,895

(22) Filed: May 24, 2002

(65) Prior Publication Data

US 2002/0188285 A1 Dec. 12, 2002

Related U.S. Application Data

(60) Provisional application No. 60/296,477, filed on Jun. 8, 2001.

(51) Int. Cl.[7] .............................................. A61B 18/18
(52) U.S. Cl. .............................. 606/15; 606/2.5; 606/7; 606/20; 606/78; 600/101; 600/143
(58) Field of Search ........................ 606/2.5, 7, 13–17, 606/20, 76, 78; 607/88, 89; 604/21, 22, 27, 34; 600/101, 104–109, 114, 117, 118, 122, 123, 129–131, 135, 137, 139, 143–152

(56) References Cited

U.S. PATENT DOCUMENTS

| | | | |
|---|---|---|---|
| 4,261,644 A | | 4/1981 | Giannaris |
| 4,930,494 A | * | 6/1990 | Takehana et al. ........... 600/145 |
| 5,114,402 A | * | 5/1992 | McCoy ..................... 604/95.05 |
| 5,645,520 A | * | 7/1997 | Nakamura et al. .......... 600/151 |
| 5,766,164 A | | 6/1998 | Mueller et al. |
| 5,860,914 A | * | 1/1999 | Chiba et al. ................ 600/151 |
| 6,039,727 A | | 3/2000 | Javier, Jr. et al. |
| 6,066,131 A | | 5/2000 | Mueller et al. |
| 6,110,164 A | | 8/2000 | Vidlund |
| 6,162,214 A | | 12/2000 | Mueller |
| 6,240,231 B1 | | 5/2001 | Ferrera et al. |
| 6,344,037 B1 | | 2/2002 | Suorsa et al. |
| 6,458,076 B1 | * | 10/2002 | Pruitt ........................ 600/146 |

* cited by examiner

*Primary Examiner*—A. Farah
(74) *Attorney, Agent, or Firm*—Bacon & Thomas, PLLC

(57) ABSTRACT

A mechanism and method for steering a surgical instrument inserted into an endoscope such as a ureteroscope, nephroscope, or cystoscope, and/or for steering the endoscope, utilizes a shape memory structure secured to the surgical instrument or to the endoscope, the shape memory structure having a transformation temperature slightly greater than that of the human body so that bending of the shape memory structure, and therefore of the surgical instrument or endoscope, may be carried out by raising a temperature of irrigation fluid in the working channel. The steering mechanism may be used as a supplement to a tensioned-wire steering mechanism, reducing stress on the endoscope shaft and extending the service life and repair interval of the endoscope. In addition, when the surgical instrument is a glass optical fiber, the steering mechanism may be used to ensure that a tip of the optical fiber is within the field-of-view of fiber optics incorporated into the endoscope.

28 Claims, 5 Drawing Sheets

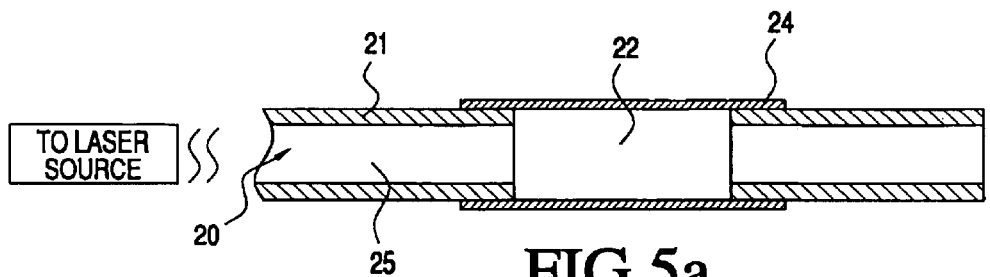
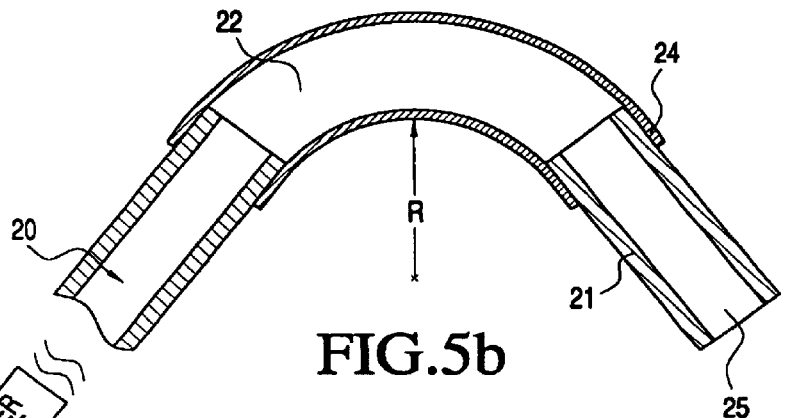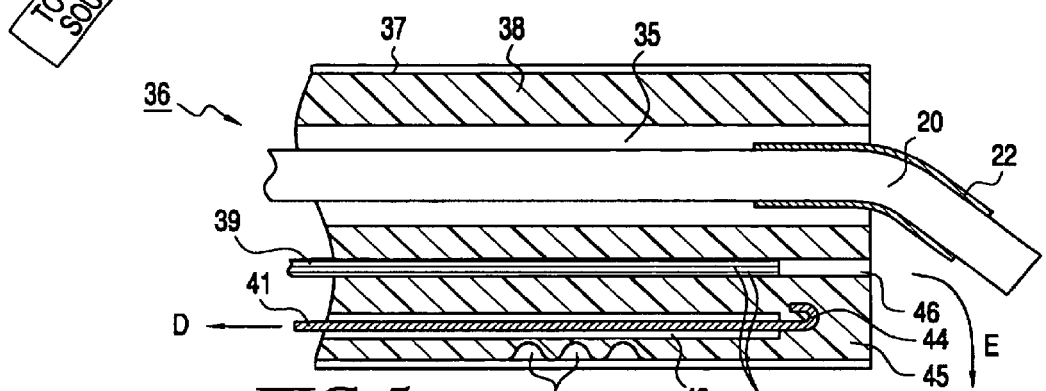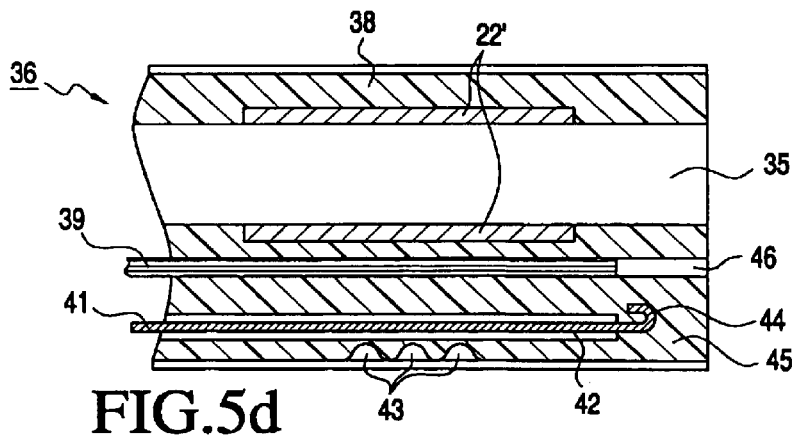

DEFLECTION MECHANISM FOR A SURGICAL INSTRUMENT, SUCH AS A LASER DELIVERY DEVICE AND/OR ENDOSCOPE, AND METHOD OF USE

This application claims the benefit of U.S. Provisional Application Ser. No. 60/296,477 filed Jun. 8, 2001.

BACKGROUND OF THE INVENTION

1. Field of the Invention

This invention relates to a mechanism for deflecting a surgical instrument inserted into an endoscope, and/or a distal end of the endoscope shaft, and to a method of causing the distal end of the surgical instrument and/or endoscope shaft to bend during a surgical procedure. The invention also relates to a self-steering laser fiber.

Although not necessarily limited to a particular surgical application, the invention is especially suitable for use in deflecting the end of a urological endoscope such as a ureteroscope, nephroscope, or cystoscope, in order to direct a surgical laser at a kidney stone for the purpose of fragmenting the stone.

According to a first preferred embodiment of the invention, a mechanism is provided for deflecting a laser-delivery glass optical fiber inserted into the working channel of the endoscope to reduce strain on a conventional tensioned-wire shaft deflection mechanism, and for keeping the end of the glass fiber in the field-of-view of an optical fiber bundle embedded in the endoscope. In this embodiment, the deflecting mechanism is a sleeve which surrounds an end of the laser-delivery fiber and which includes a shape memory alloy having a transformation temperature slightly higher than body temperature. When an appropriate fluid such as water having a temperature corresponding to the transformation temperature of the shape memory alloy is supplied to the working channel, the sleeve assumes a predetermined bent shape to deflect the end of the fiber.

According to a second preferred embodiment of the invention, the deflecting mechanism is a sleeve embedded in the shaft of the endoscope, the sleeve again including a shape memory alloy having a transformation temperature slightly higher than body temperature so as to bend and thereby deflect the end of the shaft when a fluid having a temperature greater than or equal to the transformation temperature is supplied to the working channel. The deflecting mechanism of this embodiment may supplement or replace the conventional tensioned-wire deflecting mechanism.

2. Description of Related Art

Over the past 25 years, the field of medical endoscopy has substantially matured. Today, surgeons can not only use endoscopes to view inside of hollow organs, such as the urethra and rectum, without the need to make incisions, but they can also extract tissue samples for subsequent biopsy or use the endoscope to guide an optical fiber that can deliver intense laser radiation to accomplish surgical functions such as cutting or cauterizing tissue or fragmenting kidney stones.

Modern endoscopes used for urological applications (ureterscopes) are highly engineered instruments made by a number of suppliers including Olympus, Wolf, Stortz, and ACMI. They are relatively expensive, with purchase prices ranging from $10,000 to $15,000. Further, they are inherently delicate due to a number of stringent functional requirements that must be accommodated within a small shaft diameter (typically less then 3 mm) that is limited in size by human anatomy.

The functional requirements include (1) substantial flexibility to conform to the contours of the natural pathways in a body, (2) the ability to convey illumination from an external light source to the distal end of the endoscope (inside a body), (3) the ability to convey high quality images from inside the body to the surgeon, (4) inclusion of a hollow working channel to insert small instruments such as biopsy scissors or an optical fiber to perform laser surgery functions, and (5) means for steering the distal end of the shaft to increase the field of view.

A cross section of the shaft 1 of a modern endoscope (ureterscope) is shown in FIG. 1. The shaft 1 is made up of an outer plastic jacket 2 and a plastic extrusion 3. Plastic extrusion 3 encloses bundles 4 of very small diameter optical fibers 5 for illuminating and viewing tissues in viva, and a metal tension wire 6 situated within a clearance hole 7 for bending or curving the end of the shaft. In addition, extrusion 3 defines a working channel 8 through which surgical instruments such as biopsy scissors and laser-delivery glass optical fibers may be inserted.

FIGS. 2a and 2b show side views of the shaft 1 before and after tension is applied to the metal tension wire 6. The fiber bundles and working channel have been omitted from FIGS. 2a and 2b for purposes of illustration. The tension wire is free to move inside of clearance hole 7 along the entire length of the shaft, which in the case of a ureterscope is typically about two feet. A plurality of open wedge segments 11 are cut into the plastic extrusion 3, and the end of the wire is firmly secured to the distal tip of the endoscope, for example by molding a hook shaped end 9 of the tension wire into the plastic wall 10 of the tip. When tension is applied to wire 6 by pulling on the proximal end of the wire so that it moves within clearance 7 in the direction of arrow A relative to the endoscope, the wire pulls on the distal end of shaft 1 to which it is fixed, causing the distal end to bend in the direction permitted by the open wedge segments 11 by an angle of up to 180°. Once bent, as shown in FIG. 2b, the endoscope may be rotated by the surgeon, as indicated by arrow B, to permit viewing in any direction.

While the functionality of such endoscopes is impressive, their ruggedness is marginal. Periodic repairs are routine costing from $3,000 to $6,000. One of the major causes for failure requiring repair is due to permanent distortions in the shape of the shaft cross section caused by the tension applied to the steering wire, as shown in FIGS. 3a and 3b. FIG. 3a shows the undistorted endoscope shaft and FIG. 3b shows the distorted shaft, with the distortion being indicated by reference numeral 14. Such a distortion limits the range of angles over which the distal end of the shaft may be steered or bent to less that the desired 180 degrees.

To make matters worse, if an object is inserted into the working channel that is inherently rigid, like the large-diameter glass optical fiber used to guide laser beams for surgical functions, greater tensile forces must be applied to the steering wire to overcome the extra rigidity. This typically results in a reduction in the periodic repair interval for the endoscope that is undesirable both due to high cost and a temporary loss of use of the endoscope.

The present invention offers a means to reduce or overcome the inherent rigidity of large diameter laser-delivery optical fibers used or other instruments used in endoscopes and thereby increase the useful service period between repairs, by providing a deflection mechanism for the instrument that is separate from the endoscope shaft deflection mechanism. The invention may also be used as a supplemental means to steer the endoscope shaft, i.e., to assist the tension wire in steering, and therefore further reduce the tensile force in the steering wire and extend the periodic repair interval of endoscopes.

In addition to reducing strain on the endoscope deflection mechanism and associated distortion of the endoscope shaft, by overcoming the inherent rigidity of instruments inserted into the working channel of the endoscope and/or by providing a supplemental means of deflecting the shaft, the invention helps resolve another problem, illustrated in FIG. 4, that is experienced by surgeons who use endoscopes to perform surgery by delivering a powerful laser beam through an optical fiber inserted into the working channel. The problem is that the tip 13 of the laser-delivery fiber 12, which extends out of the working channel 8 during laser delivery, may not always be in the field of view a of the lens 14 that is conventionally provided at the end of optical fiber bundle 4 to facilitate viewing of the fiber tip 13. A surgeon must be able to view the tip 13 of the surgical fiber 12 to ensure that it is properly positioned before launching a high power laser beam into the fiber to accomplish a surgical function.

Because of the offset Y between the coherent fiber bundle 4 and the working channel 8, laser delivery fiber tip 13 must protrude some distance beyond the end 10 of shaft 1 (typically several millimeters, and up to about 5 mm). However, as shown in FIG. 4, the fiber 12 may still be unfavorably positioned as a result of random orientation of the fiber within the constraints of the working channel, which causes tip 13 to point away from the field of view. In that situation, the fiber tip may be rotated into the field of view α, but only if the laser-delivery fiber has sufficient curvature, as indicated in dashed-line by reference numerals 12' and 13'.

SUMMARY OF THE INVENTION

It is accordingly a first objective of the invention to decrease the repair interval of an endoscope and extend its useful life by providing a deflection mechanism for surgical instruments inserted into the working channel of an endoscope shaft, reducing stress on the shaft deflection mechanism and on the shaft itself.

It is a second objective of the invention to decrease the repair interval of an endoscope and extend its useful life by providing a deflection mechanism for the shaft of the endoscope, which may be used to assist or possibly replace the conventional tensioned-wire shaft deflection mechanism.

It is a third objective of the invention to provide an endoscopic laser delivery system in which the end of the laser-delivery fiber may more easily be viewed by a surgeon.

It is a fourth objective of the invention to provide a glass optical fiber for insertion into the working channel of an endoscope, in which the problems of rigidity and random movement or drift of the fiber end out of the field-of-view of the endoscope are both overcome by enabling the end of the fiber to flex during a surgical procedure.

It is a fifth objective of the invention to provide a surgical instrument deflection mechanism and/or a shaft deflection mechanism that is relatively low in cost, safe, easy-to-use, and effective.

It is a sixth objective of the invention to provide a simple and safe method of deflecting the end of a surgical instrument and/or endoscope shaft.

It is a seventh objective of the invention to provide a ureteroscope, nephroscope, or cystoscope having increased reliability.

These objectives are accomplished, in accordance with the principles of various preferred embodiments of the invention, by providing a deflection mechanism for the distal end of a surgical instrument inserted into the working channel of an endoscope, and/or for the shaft of the endoscope itself, in which bending of the instrument or shaft is carried out by means of a shape memory allow structure having the properties of being almost as flexible as the fiber alone at low temperatures, and of reverting to a curved shape at higher temperatures, with a radius of curvature less than or equal to the minimum bend radius of the endoscope.

The shape memory alloy is preferably a nickel titanium alloy, also known as NITINOL (Nickel Titanium Naval Ordnance Labs). NITINOL is commercially available from Memry Corporation of Bethel, Conn., in a range of compositions that have different transformation temperatures, i.e., temperatures at which structures containing the alloys recover their initial high temperature shape. When these alloys are formed into a shape, such as a curved hollow tube, at high temperature, they may be subsequently cooled and deformed at low temperatures, such as by straightening the hollow cylinder, and yet when heated they will recover their initial curved shape without the application of any forces. Preferably, the transformation temperature of the shape memory alloy used in connection with the present invention is just several degrees above the normal temperature of the human body so as to enable shape recovery by controlling the temperature of fluids pumped or introduced into the working channel of the endoscope.

According to a preferred method of utilizing the endoscope of the invention, a surgical instrument is inserted into the working channel of the endoscope and warm water is caused to flow around it, thereby causing the shape memory sleeve at the distal end of the surgical instrument or the distal end of the endoscope shaft to bend or curve without necessitating application of extra tensile forces on the steering wire of the endoscope. When the shape memory sleeve is provided on the surgical instrument and the endoscope shaft includes a steering wire, the surgical instrument is preferably inserted into the endoscope in such a way as to orient its shape memory curve to coincide with the bend produced by tensioning a steering wire.

According to the preferred embodiments of the invention, the surgical instrument is a laser delivery optical fiber. However, it should be appreciated that the principles of the invention are also applicable to such surgical instruments as the "baskets" used to retrieve, upon insertion into a ureteroscope, remaining particles of a kidney stone that has been fragmented by laser energy. It is within the scope of the invention to apply the shape memory sleeve to such baskets, as well as to other surgical instruments that might be inserted into an endoscope, with or without associated laser fiber working channels.

BRIEF DESCRIPTION OF THE DRAWINGS

FIGS. 5a and 5b are cross-sectional side views showing a fiber with a shape memory tube according to a first preferred embodiment of the invention.

FIGS. 5c is a cross-sectional side view showing an endoscope into which a shape-changing laser deliver fiber has been inserted according to the first preferred embodiment of the invention.

FIG. 5d is a cross-sectional side view showing an endoscope with having a shape-changing fiber incorporated into walls of the shaft according to a second preferred embodiment of the invention.

DETAILED DESCRIPTION OF THE PREFERRED EMBODIMENTS

Figure 1:
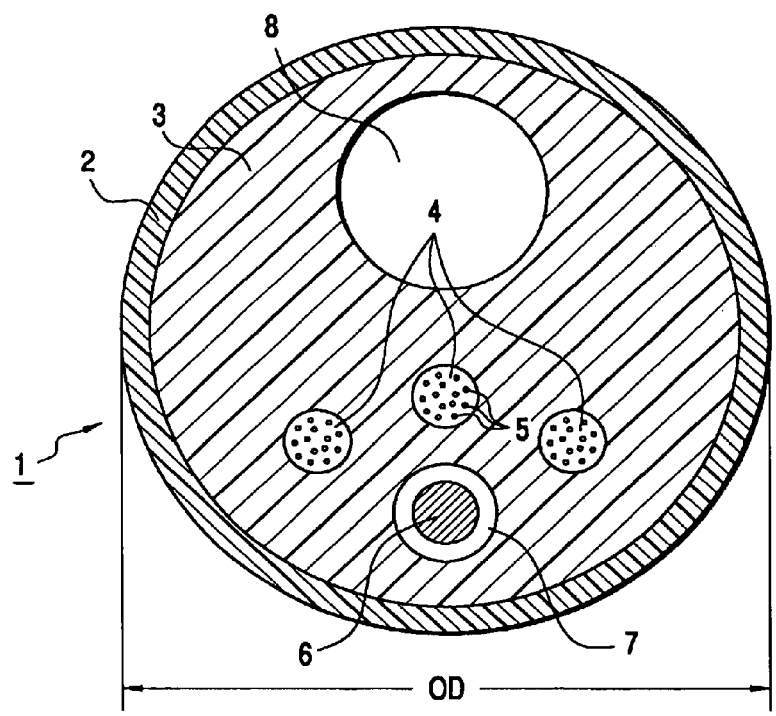
FIG. 1 is a cross-sectional end view of a conventional endoscope.
Figure 2A:
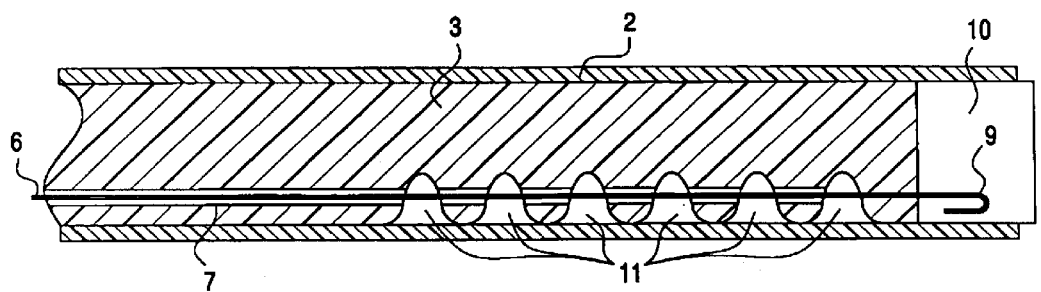
FIGS. 2a and 2b are cross-sectional side views of the endoscope of FIG. 1.
Figure 2B:
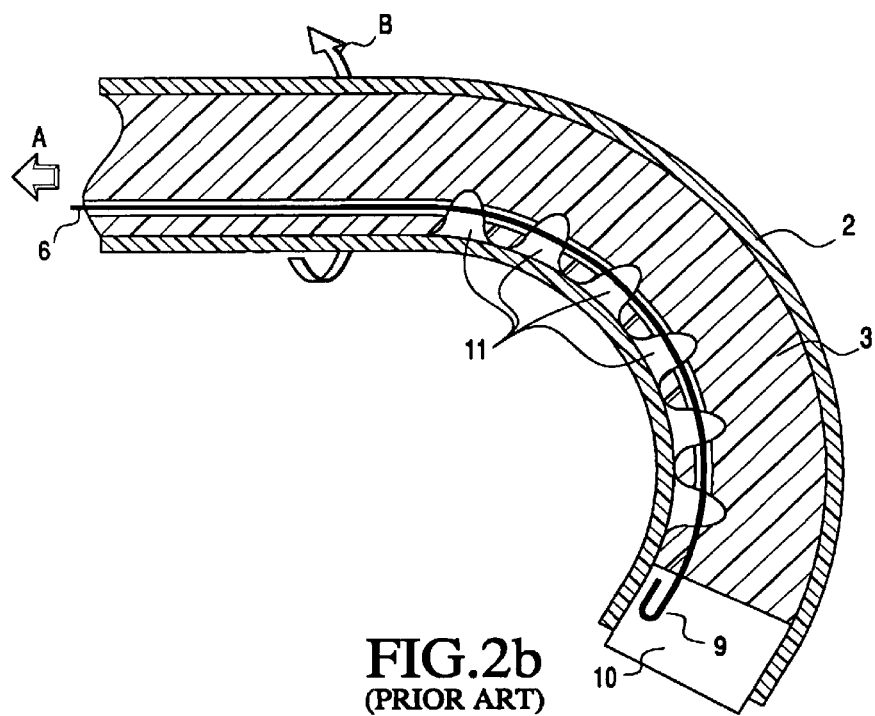
Figure 3A:
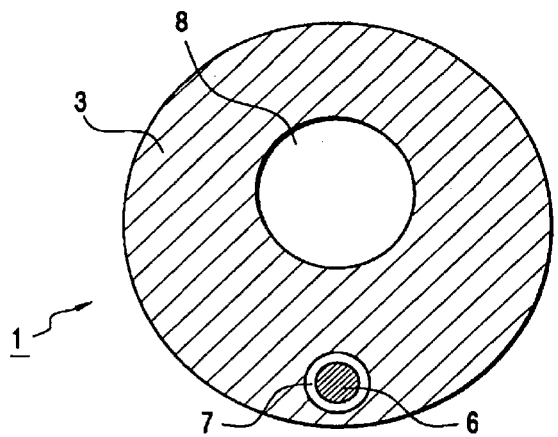
FIGS. 3a and 3b are cross-sectional end views corresponding to the end view of FIG. 1, with elements omitted.
Figure 3B:
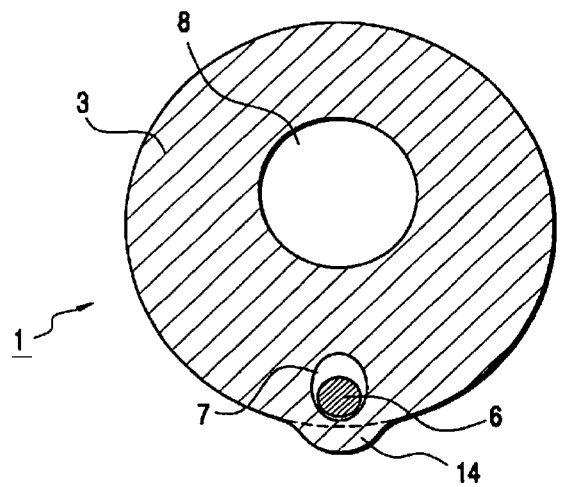
Figure 4:
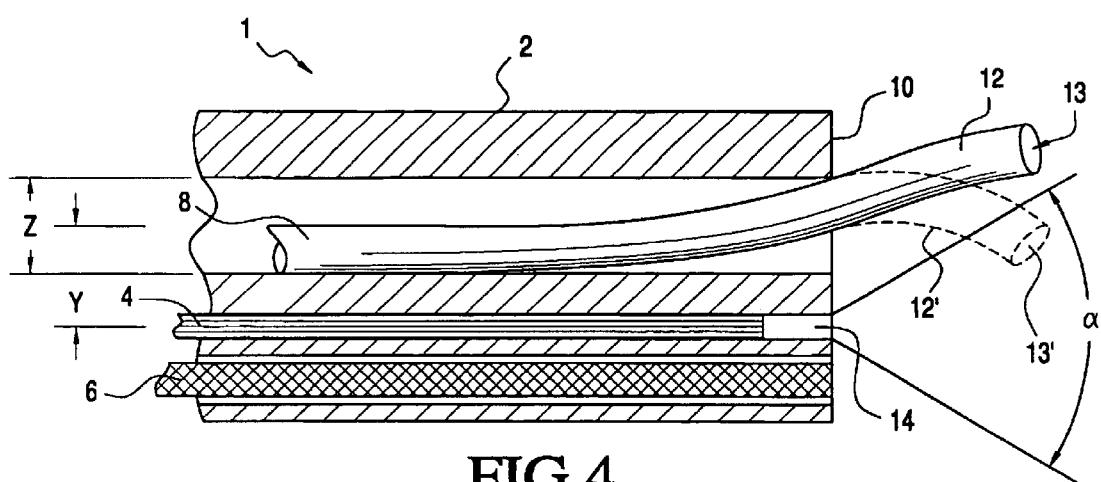
FIG. 4 is a cross-sectional side view showing the endoscope of FIG. 1 with an inserted surgical instrument in the form of a laser-delivery glass optical fiber.

As shown in FIG. 5a, an optical fiber 20 of the type used to deliver laser energy to a tissue during an endoscopic procedure includes a buffer/coating 21 and a core 25 fitted into a generally cylindrical member or sleeve 22 made of a shape memory material. Currently, the preferred shape memory material is a nickel-titanium alloy, although the invention is not necessarily limited to a particular shape memory material.

As shown in FIG. 5b, the sleeve 22 is caused to change its shape to form, for example, a centering half helix, by changing the temperature of the sleeve. According to a preferred embodiment of the invention, the change in temperature is accomplished by changing the temperature of the irrigation fluid so that it exceeds the transformation temperature of the shape memory material in sleeve 22. Preferably, the transformation temperature is no more than a few degrees above the normal temperature of the human body (98.6° F.) so that the irrigation fluid will simply be absorbed by the body without causing any damage.

Also as shown in FIGS. 5a and 5b, the sleeve may be secured to the fiber 20 by a heat shrink sleeve 24, although those skilled in the art will appreciate that the sleeve may be secured to the fiber by other means having properties that permit it to be inserted into a patient, including adhesives.

FIG. 5c shows an application of the shape-changing laser-delivery fiber arrangement illustrated in FIGS. 5a and 5b, in which the fiber is inserted into the working channel 35 of an endoscope shaft 36, such as the shaft of a ureteroscope, nephroscope, or cystoscope, corresponding to the conventional endoscope shaft illustrated in FIGS. 1–4, the shaft again being made of an outer plastic jacket 37 and a plastic extrusion 38. Plastic extrusion 38 encloses bundles 39 of very small diameter optical fibers 40 for illuminating and viewing tissues in vivo, and a metal tension wire 41 situated within and movable relative to a clearance hole 42 for bending or curving the end of the shaft. A plurality of open wedge segments 43 are cut into the plastic extrusion 38, and the end of the wire is firmly secured to the distal tip of the endoscope by molding a hook shaped end 44 of the tension wire 41 into the plastic wall 45 of the tip. When tension is applied to wire 41 by pulling on the proximal end of the wire so that it moves within clearance 42 in the direction of arrow D relative to the endoscope, the wire pulls on the distal end of shaft 36 to which it is fixed, causing the distal end to bend in the direction of arrow E permitted by the open wedge segments 43. In addition, upon raising the temperature of the irrigation fluid to the transformation temperature, the laser deliver fiber 20 is also bent in direction E, reducing the amount by which the endoscope needs to be bent in order to achieve a total deflection of up to 180°, and bringing the tip of the fiber into the field of view of lens 46 at the termination of fiber bundles 39.

In the second preferred embodiment of the invention, the shape memory sleeve is molded into or otherwise secured directly within or to the endoscope shaft 36, so as to supplement the tension wire bending mechanism. As illustrated in FIG. 5d, the shape memory sleeve 22' is simply molded into the plastic extrusion 38. Elements common to FIGS. 5c and 5d are designated by the same reference numerals.

It will be appreciated by those skilled in the art that in this embodiment, the wire bending mechanism may be eliminated entirely and the directly attached or integrated shape mechanism used as the sole means of steering the tip of the endoscope. In addition, the shape memory element need not necessarily be a sleeve, but rather could be non-cylindrical in shape.

Figure 6A:
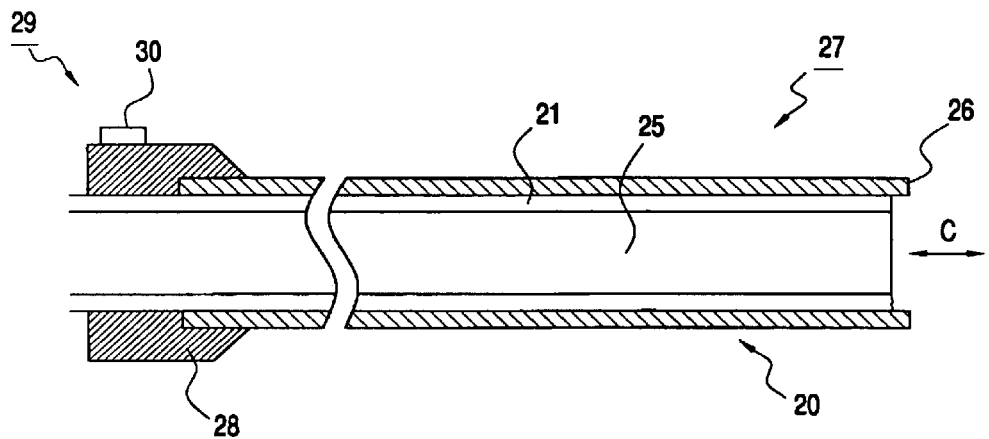
FIG. 6a is a cross-sectional side view of a fiber and sleeve structure in accordance with a variation of the first preferred embodiment of the invention.
Figure 6B:
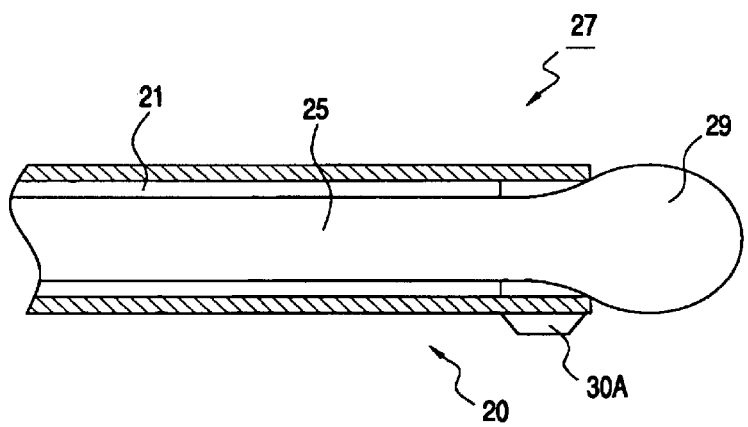
FIG. 6b is a cross-sectional side view of a fiber and sleeve structure in accordance with a further variation of the first preferred embodiment of the invention.

In the variation of the first preferred embodiment illustrated in FIG. 6a, the shape memory sleeve 22 is extended towards the proximal end 29 of the endoscope, i.e., towards the laser, and is adjustably coupled to the laser-delivery fiber 20 by a pin vice mechanism 28 at the proximal end of the fiber. Pin vice mechanism 28 permits adjustment of the fiber relative to the sleeve in the direction of arrow C so as to enable the fiber to be re-cleaved for reuse. Since sleeve 22 extends, at least initially, beyond the distal end 27 of the fiber, it preferably includes a beveled or rounded edge 26 at the distal end to prevent damage to the working channel of an endoscope shaft into which the fiber and sleeve are inserted. Alternatively, for single use applications, the fiber could extend beyond the sleeve 22 and the fiber tip 39 could also be beveled or rounded, as illustrated in FIG. 6b. The beveled or ball tip fiber may be made using a laser, fusion splicer, or flame, all of which will fire polish the surface, resulting in a fire-polished fiber tip that is stronger than a flat polished or cleaved tip.

As illustrated in FIG. 6a, an index tab 30 at the proximal end 29 of the fiber 20 may be used to indicate the direction that the sleeve 22 will bend when the temperature of the irrigation fluid exceeds the transformation temperature of the shape memory material, thereby facilitating rotation of the fiber within the endoscope. In addition, as illustrated in FIG. 6b, another tab or line indicator 30A may be placed on the sleeve 22 at the distal end 27 of the fiber so that the surgeon can see placement inside the endoscope.

In order to provide maximum flexibility and permit the scope to make sharp bends, it is desirable to use very small fibers. For example, fibers having cores as small as 200 microns are typically used for Holmium laser lithotripsy. However, those skilled in the art are advised that since the laser focused spot on the proximal surface is typically 250 microns or more, excess laser energy may travel down the fiber outer cladding and, if high enough, burn the outer coating of the fiber and the working channel of the scope should the fiber be bent too far.

By way of example and not limitation, a glass laser-delivery optical fiber arrangement constructed in accordance with the principles of the first embodiment of the invention may have the following specific structure and dimensions: The fiber has an outside glass diameter of 326 microns (0.326 mm) and is covered with a polymer buffer layer with an outside diameter of 400 microns (0.400 mm) positioned inside of a hollow NITINOL tube having an inside diameter of 450 microns and an outside diameter of 600 microns. At low temperatures, this structure is almost as flexible as the fiber alone, yet at temperatures several degrees above body temperature the end section of the nickel-titanium alloy tube reverts to a curved shape initially formed at high temperature, with a radius of curvature less than or equal to the minimum bend radius of an endoscope. When this fiber-sleeve assembly is inserted into the working channel of a urological endoscope there is sufficient clearance between the 1.2 mm diameter of the channel and the 0.6 mm diameter of the nickel-titanium alloy sleeve to flow warm water around it and cause the fiber-tube assembly to take on a curved shape without requiring extra tensile forces on the steering wire in the endoscope, and effectively overcoming the inherent rigidity of the fiber. Preferably, the fiber-sleeve assembly has been inserted into the endoscope in such a way as to orient its shape memory curve to coincide with the bend produced by tensioning the steering wire.

When this fiber-tube assembly is used with an endoscope having metal tension wires of the type illustrated in FIG. 1, the warm water (above the nickel-titanium alloy transformation temperature) is pumped down the working channel around the fiber and sleeve while the surgeon applies tension to the steering wires in the endoscope. The warm water flows out of the distal end of the endoscope and eventually is voided from the patient's body by flowing outside the endoscope shaft. By following such a procedure, the tensile force in the steering wire is reduced and the service life and interval between repairs of the endoscope will increase.

A properly oriented fiber-NITINOL alloy tube assembly causes the fiber to curve towards to the tension wire in order to reduce the applied tensile stress in the wire. It can be seen in FIGS. 4 and 5c that curvature of the fiber in this direction also causes its end to curve into the field of view of the coherent fiber bundle through which the tip of the fiber is viewed. This substantially helps resolve the often-experienced problem that the surgeon cannot see the tip of the fiber.

Having thus described a preferred embodiment of the invention in sufficient detail to enable those skilled in the art to make and use the invention, it will nevertheless be appreciated that numerous variations and modifications of the illustrated embodiment may be made without departing from the spirit of the invention, and it is intended that the invention not be limited by the above description or accompanying drawings, but that it be defined solely in accordance with the appended claims.

We claim:

1. A surgical endoscope, comprising:
   a shaft having a working channel formed therein;
   a surgical instrument inserted into the working channel, said surgical instrument being at least partially surrounded by a shape memory structure arranged to transform to a curved shape at a transformation temperature that is a few degrees higher than body temperature and thereby steer said surgical instrument, said shape memory structure being bathed by an irrigation fluid supplied to the working channel of the shaft, a temperature of said irrigation fluid determining when said shape memory structure will transform to a curved shape and thereby enable steering of said surgical instrument, a temperature of said irrigation fluid being near body temperature before and after transformation to a curved shape so that the irrigation fluid will be absorbed by a body of a patient without causing any damage.

2. A surgical endoscope as claimed in claim 1, wherein said surgical instrument is a glass optical fiber arranged to have a laser surgical function, and said shape memory structure is secured to said glass optical fiber.

3. A surgical endoscope as claimed in claim 1, wherein said surgical endoscope is a urological endoscope.

4. A surgical endoscope as claimed in claim 3, wherein said surgical endoscope is selected from the group consisting of a ureteroscope, nephroscope, and cystoscope.

5. A surgical endoscope as claimed in claim 1, wherein the shape memory structure is a hollow sleeve secured to and surrounding said surgical instrument.

6. A surgical endoscope as claimed in claim 1, wherein the surgical instrument is a basket adapted to remove fragmented kidney stones.

7. A surgical endoscope as claimed in claim 6, wherein said shape memory structure is secured to said surgical instrument by a heat shrink sleeve.

8. A surgical endoscope as claimed in claim 1, further comprising a steering wire, and wherein said shape memory structure is positioned within said endoscope such that a curvature of said shape memory structure is in a same direction as a curvature of the endoscope caused by applying tension to the steering wire.

9. A surgical endoscope as claimed in claim 8, wherein positioning of the instrument within the endoscope is facilitate by an index marker at a proximal end of the endoscope.

10. A surgical endoscope as claimed in claim 1, wherein said shape memory structure is a sleeve that surrounds said surgical instrument and that is secured to said surgical instrument by a pin vise arranged to permit adjustment of a position of said surgical instrument within said shape memory structure.

11. A surgical endoscope as claimed in claim 10, wherein a distal end of the shape memory structure is beveled to eliminate sharp edges that could damage an inner wall of the working channel.

12. A surgical endoscope as claimed in claim 10, wherein the surgical instrument is an optical fiber, and a distal end of the optical fiber is rounded.

13. A surgical endoscope as claimed in claim 10, wherein an index mark is included at a distal end of the surgical instrument to permit viewing of a position of the instrument through the endoscope.

14. A surgical endoscope as claimed in claim 1, wherein said shape memory structure is incorporated into walls of a shaft of the endoscope.

15. A surgical endoscope as claimed in claim 1, wherein said shape memory structure is made of a nickel-titanium alloy.

16. A laser-delivery device arranged to be inserted into a working channel of an endoscope and to deliver laser energy to tissues in vivo, comprising:
    a glass optical fiber, said glass optical fiber being at least partially surrounded by a shape memory structure having a transformation temperature a few degrees higher than a temperature of a body into which the endoscope is inserted, said shape memory structure being secured directly to said glass optical fiber, wherein a transformation temperature of said shape memory alloy is a few degrees higher than body temperature and a temperature of said irrigation fluid being near body temperature before and after transformation to said curved shape so that the irrigation fluid will be absorbed by a body of the patient without causing any damage.

17. A laser-delivery device as claimed in claim 16, wherein the shape memory structure is a hollow sleeve secured to and surrounding said glass optical fiber.

18. A laser-delivery device as claimed in claim 16, wherein said shape memory structure is secured to said glass optical fiber by a heat shrink sleeve.

19. A laser-delivery device as claimed in claim 16, wherein positioning of the instrument within the endoscope is facilitated by an index marker at a proximal end of the endoscope.

20. A laser-delivery device as claimed in claim 16, wherein an index mark is included at a distal end of the surgical instrument to permit viewing of a position of the instrument through the endoscope.

21. A laser-delivery device as claimed in claim 16, wherein said shape memory structure is secured to said surgical instrument by a pin vise arranged to permit adjustment of a position of said surgical instrument within said shape memory structure.

22. A laser-delivery device as claimed in claim 21, wherein a distal end of the shape memory structure is beveled to eliminate sharp edges that could damage an inner wall of the working channel of the endoscope into which the laser-delivery device is inserted.

23. A laser-delivery device as claimed in claim 21, wherein a distal end of the optical fiber is rounded.

24. A laser-delivery device as claimed in claim 16, wherein said shape memory structure is made of a nickel-titanium alloy.

25. A method of orienting a surgical instrument inserted into a working channel of an endoscope, comprising the step of raising a temperature of irrigation fluid in the working channel to cause a shape memory structure at an end of the surgical instrument to transform to a predetermined curved shape, wherein a transformation temperature of said shape memory alloy is a few degrees higher than body temperature and a temperature of said irrigation fluid being near body temperature before and after transformation to said curved shape so that the irrigation fluid will be absorbed by a body of the patient without causing any damage.

26. A method as claimed in claim 25, further comprising the step of pulling on a tension wire to cause a distal end of a shaft of the endoscope to curve.

27. A method as claimed in claim 26, further comprising the step of inserting the surgical instrument into the working channel of the endoscope and orienting the surgical instrument using an index marker so that a curvature of the surgical instrument following transformation is in a same direction as a curvature of the endoscope following the step of pulling on the tension wire.

28. A surgical instrument, comprising:
a shaft having a working channel formed therein, said shaft including a first end arranged to be inserted into a patient and a second end extending outside the patient when the first end is inserted into the patient; and
a shape memory structure situated near said first end and arranged to be selectively bathed by an irrigation fluid having a temperature that causes said shape memory structure to transform to a curved shape and thereby enable steering of said shaft, a transformation temperature of said shape memory alloy being a few degrees higher than body temperature and a temperature of said irrigation fluid being near body temperature before and after transformation to a curved shape so that the irrigation fluid will be absorbed by a body of the patient without causing any damage.

* * * * *